(12) United States Patent
Garnaik

(10) Patent No.: US 9,150,609 B2
(45) Date of Patent: Oct. 6, 2015

(54) PROCESS FOR THE PREPARATION OF COPOLYMER-1 USING A POLYMER SUPPORTED DIALKYLAMINE INITIATOR

(75) Inventor: Baijayantimala Garnaik, Pune (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 776 days.

(21) Appl. No.: 13/375,914

(22) PCT Filed: Jun. 4, 2009

(86) PCT No.: PCT/IN2009/000320
§ 371 (c)(1),
(2), (4) Date: Dec. 2, 2011

(87) PCT Pub. No.: WO2010/140157
PCT Pub. Date: Dec. 9, 2010

(65) Prior Publication Data
US 2012/0077952 A1    Mar. 29, 2012

(51) Int. Cl.
*C07K 1/00* (2006.01)
*A61K 8/64* (2006.01)
*A61K 38/00* (2006.01)
*C07K 14/00* (2006.01)

(52) U.S. Cl.
CPC ... *C07K 1/00* (2013.01); *A61K 8/64* (2013.01); *A61K 38/00* (2013.01); *C07K 14/001* (2013.01)

(58) Field of Classification Search
CPC .............. C07K 1/00; A61K 8/64; A61K 38/00
USPC ........ 424/78.08; 514/561, 1.1, 17.9; 525/419; 530/333
IPC ......... A61K 31/785, 38/00; C08L 79/08; C07K 14/4713, 1/02
See application file for complete search history.

(56) References Cited

U.S. PATENT DOCUMENTS

| | | |
|---|---|---|
| 3,849,550 A | 11/1974 | Teitelbaum et al. |
| 5,981,589 A | 11/1999 | Konfino et al. |
| 6,620,847 B2 | 9/2003 | Konfino et al. |
| 7,279,172 B2 | 10/2007 | Aharoni et al. |

FOREIGN PATENT DOCUMENTS

| | | |
|---|---|---|
| WO | 9531990 | 11/1995 |
| WO | 2007022193 A2 | 2/2007 |

OTHER PUBLICATIONS

International Search Report for International Application No. PCT/IN2009/000320 dated Dec. 18, 2009.

*Primary Examiner* — David Lukton
(74) *Attorney, Agent, or Firm* — Abelman, Frayne & Schwab

(57) ABSTRACT

A process for the synthesis of copolymer-1 composed of L-alanine, L-lysine, L-glutamic acid and L-tyrosine for the treatment of multiple sclerosis. The molecular weight of copolymer-1 is between 8-19 KDa. The process is initiated by supported dialkyl amine. The copolymer-1 of the invention has acid content of less than 1%.

5 Claims, 6 Drawing Sheets

PROCESS FOR THE PREPARATION OF COPOLYMER-1 USING A POLYMER SUPPORTED DIALKYLAMINE INITIATOR

This application is a 371 of PCT/IN2009/000320, filed Jun. 4, 2009.

FIELD OF THE INVENTION

The present invention relates to a process for the synthesis of Copolymer-1 (Cop I). composed of L-alanine, L-lysine, L-glutamic acid and L-tyrosine for the treatment of multiple sclerosis.

BACKGROUND AND PRIOR ART

Copolymer-1 is a synthetic peptide analog of myelin basic protein (MBP), which is a natural component of myelin sheath. It is a non-autoantigen, which suppresses experimental allergic encephalomyelitis (EAE) induced by various encephalitogens including mouse spinal cord homogenate, which includes all myelin antigens such as myelin basic protein. Copolymer-1 has been demonstrated to be active when injected subcutaneously, intra-peritoneally, intravenously or intramuscularly. It is known that Copolymer-1 is used in the treatment of multiple sclerosis.

Reference may be made to U.S. Pat. No. 3,849,550 wherein they claim a process wherein the N-carboxyanhydrides (NCA) of tyrosine, alanine, γ-benzyl glutamate and $N^{\epsilon}$-trifluoro-acetyl lysine are polymerized at ambient temperature in anhydrous dioxane with diethylamine as initiator.

Reference may be made to U.S. Pat. No. 5,800,808 wherein they claim a method of manufacturing copolymer-1, comprising reacting protected copolymer-1 with hydrobromic acid to form trifluoroacetyl copolymer-1, treating said trifluoroacetyl copolymer-1 with aqueous piperidine solution to form copolymer-1, and purifying said copolymer-1, to result in copolymer-1 having a molecular weight of about 5 to 9 kilodaltons.

Reference may be made to U.S. Pat. No. 5,981,589 wherein they claim a process for the manufacture of copolymer-I, comprising reacting protected copolymer-I with hydrobromic acid to form trifluoroacetyl copolymer-I, treating the said trifluoroacetyl copolymer-I with aqueous piperidine solution to form copolymer-I and purifying said copolymer-1, to result in copolymer-1 having a molecular weight of about 5 to 9 kilodaltons. The method involves use of non-supported diethylamine as initiator.

Reference may be made to U.S. Pat. No. 3,849,550 wherein they claim a process for the preparation of a polypeptide-I composed of the following amino acid units in the structure namely: L-alanine, L-glutamic acid, L-lysine and L-tyrosine randomly arranged in the polypeptide comprising polymerization of a mixture of the N-carboxyanhydrides of L-alanine, L-tyrosine, a protected L-glutamate and a protected L-lysine to obtain protected copolymer-6 or salts thereof.

But the prior art documents do not present a process for the synthesis of co-polymer-I with control over specific molecular weight range. Further, in the prior art processes it is observed that when polymers are isolated from amine-initiated polymerization reaction mixtures and carefully freed from unreacted anhydrides, they have residual levels of acid groups titratable by sodium methoxide in various anhydrous solvents, as cited in sela et al in J. Am. Chem. Soc. Apr. 5, 1955, volume 77, page 1893-1898. Also, U.S. Pat. No. 6,620,847 has shown in example 2 that when the % of high molecular weight of co-polymer-1 species is less than 2.5%, the % release of serotonin, indicative of toxicity is low, and vice-versa. Further in the same example the inventors have specified that the copolymer with average molecular weight of 22 KDa was designated toxic.

Thus there exists a need in the art to have a process for the synthesis of co-polymer 1 wherein the molecular weight of co-polymer is controlled below 22 KDa, preferably below 20 KDa to overcome toxicity related issues. Also, the process should result in the co-polymer 1 product without the residual levels of acids. Further the process should be simple and efficient, using commonly available chemicals and result in the product directly, with a high degree of purity, not requiring any more steps to for separation, purification, fractionation of various molecular weight ranges and such like.

Novelty of the present invention lies in the process of preparation of Copolymer-I using polymer bound catalyst as initiator. The Copolymer-I obtained in the present invention has acid content of less than 1%.

OBJECTS OF INVENTION

The main objective of the present invention is to provide a process for the synthesis of co-polymer 1 useful in the treatment of multiple sclerosis that result in co-polymer 1 with control over molecular weight below 20 KDa.

Another objective of the invention is to provide a process for the synthesis of co-polymer 1 that results in co-polymer 1 with control over molecular weight below 20 KDa using chemicals that are generally available.

Yet another objective of the invention is to provide a process for the synthesis of co-polymer 1 useful in the treatment of multiple sclerosis that result in co-polymer 1 with control over molecular weight below 20 KDa, wherein the co-polymer has no residues of acids.

SUMMARY OF THE INVENTION

A process for the synthesis of copolymer-1 of molecular weight 8-19 KDa initiated by supported dialkyl amine is disclosed. The copolymer-1 of the invention has acid content of less than 1%.

Accordingly the present invention relates to a process for the synthesis of copolymer-1 having a molecular weight below 20 KDa, wherein the polymerization process is characterized in using polymer supported dialkyl amine as initiator, the said process comprising:

a. dissolving N-carboxyanhydrides (NCA) of tyrosine, alanine, γ-benzyl glutamate and $N^{\epsilon}$-trifluoroacetyllysine in a solvent;

b. polymerizing the NCA by initialization with polymer supported dialkyl amine followed by stirring at room temperature to obtain copolymer-I;

c. pouring the copolymer-I as obtained in step (b) into water, filtering the product followed by washing with water and drying;

d. suspending the dried copolymer-I as obtained in step (c) in acetic acid, adding HBr in acetic acid, stirring at room temperature, decanting and evaporating;

e. dispersing the product as obtained in step (d) in water, adding IM piperidine, stirring for a time period in the range of 20-28 hrs at room temperature;

f. dialyzing the solution as obtained in step (e) at room temperature to achieve pH=8;

g. dialyzing the solution having pH=8 as obtained in step (f) against acid followed by water to achieve pH=5.5-6 followed by concentrating the solution to obtain concentrated copolymer-I;

h. lyophilizing the solution as obtained in step (g) to dryness.

In an embodiment of the present invention the said solvent is selected from group comprising dimethyl formamide, dimethyl sulphoxide, dichloro methane, dioxane, alone and optionally in combinations thereof.

In another embodiment of the present invention the supported dialkylamine used as initiator is selected from the group comprising dimethylamine, diethylamine and diisopropylamine, alone and optionally in combinations thereof.

In yet another embodiment of the present invention the supported initiator is trialkyl amines, alone and optionally in combination with said diaklyamines.

In yet another embodiment of the present invention the copolymer-I is useful in the treatment of autoimmune diseases such as multiple sclerosis.

DETAILED DESCRIPTION OF DRAWING

In FIG. 1, elution volume (in µL) is plotted against refractive index (in au) to show that the molecular weight of the copolymer-1 synthesized by the process of the invention is between 8-19 KDa.

DETAILED DESCRIPTION OF THE INVENTION

Figure 1:
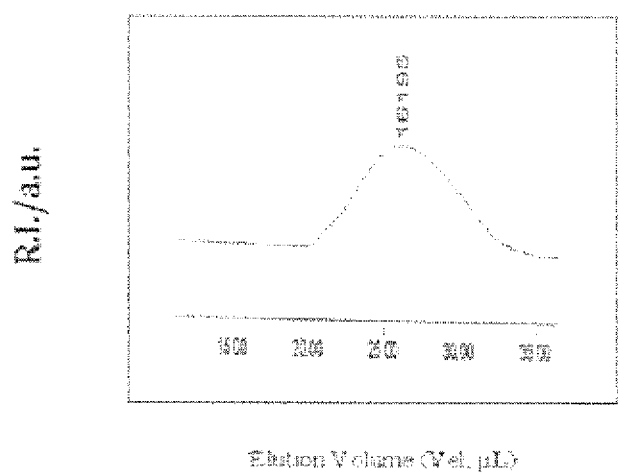
Figure 2:
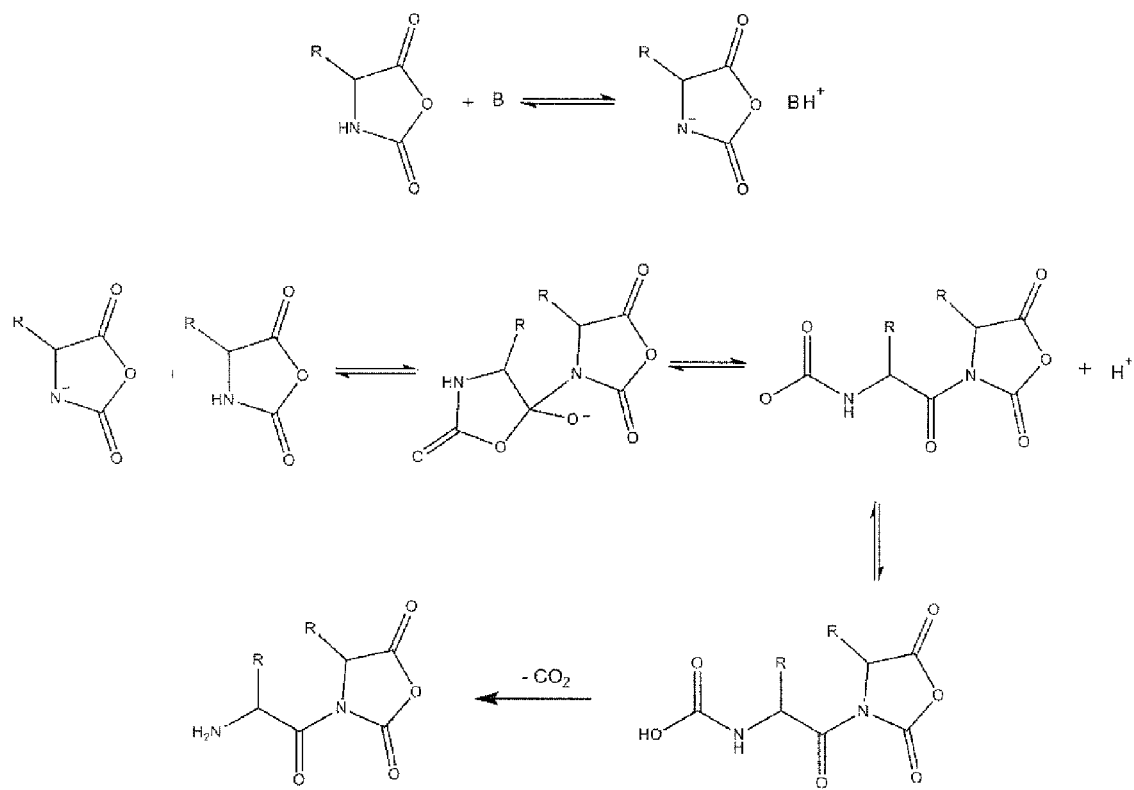
FIG. 2 represents the initiation of the process scheme of the present invention.
Figure 3:
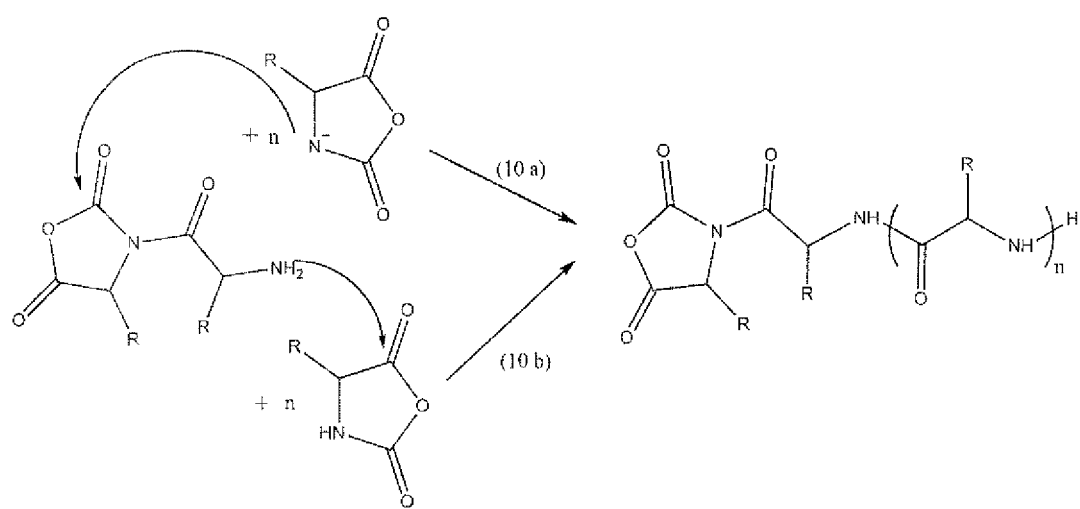
FIG. 3 represents the propagation of the process scheme of the present invention.
Figure 4:
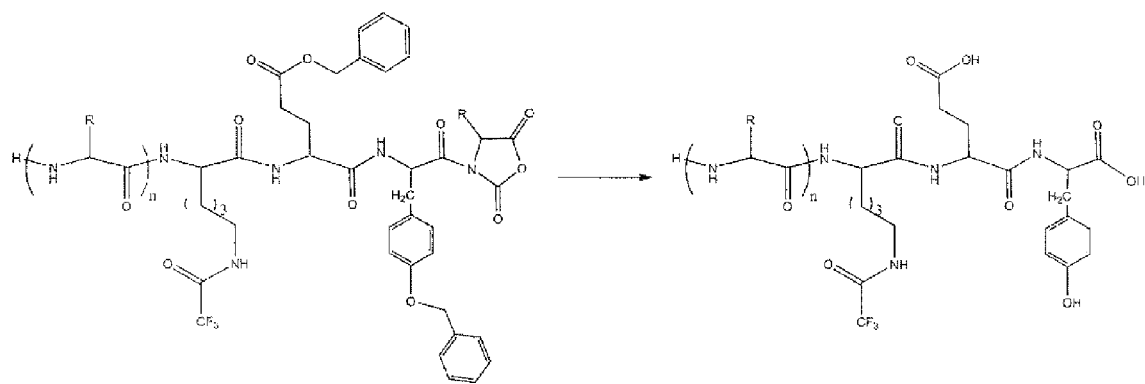
FIG. 4 represents the deprotection of γ-benzylglutamate and O-benzyl tyrosine pursuant to the process scheme of the present invention.
Figure 5:
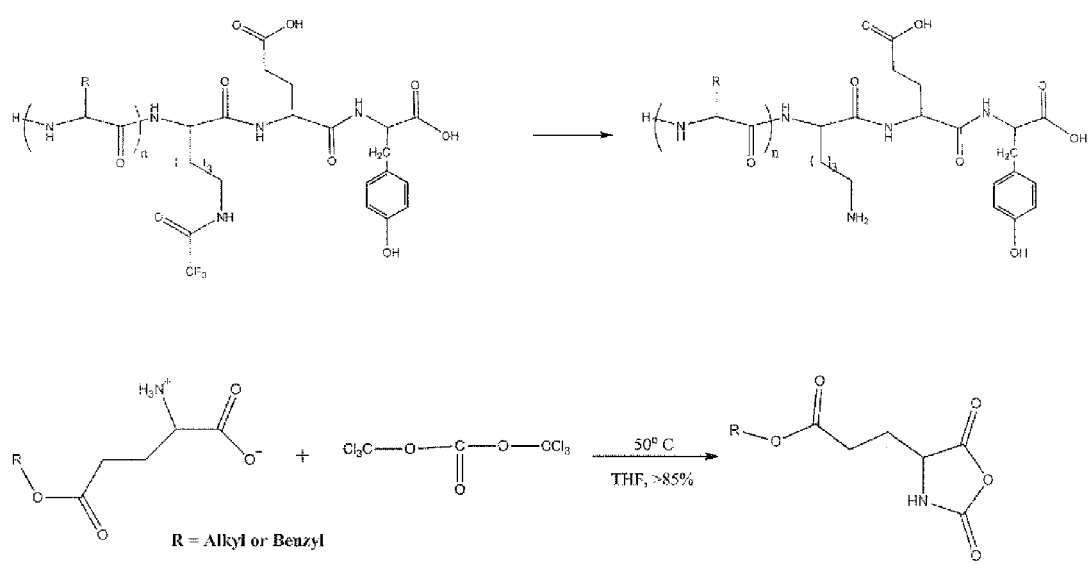
FIG. 5 represents the deprotection of N Triflouroacetyl Lysine pursuant to the process scheme of the present invention.
Figure 6:
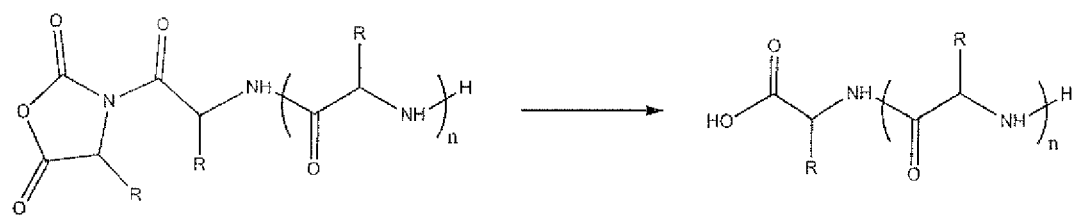
FIG. 6 represents the termination of the process scheme of the present invention, the dialkyl initiators of the invention were selected from dimethylaminer, diethylamine, diisopropylamine, and such like, alone or in combination thereof.

In the process of the invention to synthesize copolymer-1, the inventors tried with dialkyl amine initiators for the polymerization of NCAs of tyrosine, alanine, glutamate and lysine. It was surprisingly found that when the initiators are supported, the process resulted in copolymer-1 in the molecular range below 20 KDa, preferably in the range of 8 to 19 KDa.

The polymer supports were used consisting both aromatic and aliphatic monomers and comonomers, which are illustrated below:
1) Styrene-butadiene
2) Styrene-ethylene copolymer
3) Styrene-propylene copolymer
4) Styrene-d-methyl styrene
5) p-styryl diphenylphosphine copolymer catalyst support
6) Laurulated polyethyleneimine Several types of macro porous styrene-divinyl benzene copolymer (SDVB) were synthesized and selected as support materials. These materials were prepared by general procedures such as suspension polymerization, emulsion polymerization and inverse emulsion polymerization published by the authors.[1,2] SDVB was synthesized to get a porous structure. Toluene was used as a good solvent, and n-heptane or methyl methacrylate or 2-ethyl-1-hexnol as a poor solvent. The specific surface area and pore volume could be controlled by rates of monomer to solvent. This polymer support has a form of various sizes such as powdery samples, spherical, oval and cylindrical pellet etc.

The prepared supported catalyst is thermally stable up to 400 to 600° C. The physical properties of polymer supports such as BET surface area pore volume and pore size distribution etc. were measured by physical adsorption of $N_2$ gas at liquid nitrogen temperature of 77 K. using autosorb-6 (Quantachrom, USA). BET surface area various from 50 to 1000 $m^2/g$, micro porous area ~25 to 200 $m^2/g$, mesoporous area ~100 to 300 $m^2/g$, micro pore volume ranging from 0.0001 to 0.5 c.c./g, and average pore radius starting from 10 A° to 70 A°.

The amines such as primary, secondary, tertiary amines (straight chain) were linked to SDVB polymer support by chemical reaction forming covalent bonds with amines. Similarly branched amines of all three types (mentioned above) were attached to polymer support using chemical reactions. The above amines were also adsorbed on the surface of polymer supports and used.

The process of the invention comprises:
a. Dissolving N-carboxyanhydrides of tyrosine, alanine, γ-benzyl glutamate and $N^\epsilon$-trifluoroacetyllysine in a solvent;
b. Polymerizing the NCA by initialization with supported dialkylamine and stirring at room temperature;
c. Pouring the copolymer 1 formed into water, filtering the product and washing with water and drying;
d. Suspending in acetic acid, adding HBr in acetic acid, stirring at room temperature, decanting and evaporating;
e. Dispersing in water, adding 1 M piperdine, stirring for 24 hours at room temperature;
f. Dialyzing at room temperature to achieve pH; 8
g. Dialyzing against acid followed by water to achieve pH 5.5-6 and
h. Lyophilizing solution to dryness.

The process scheme is as shown in FIGS. 2, 3, 4, 5 and 6 herein.

The dialkyl amine initiators of the invention are selected from dimethylamine, diethylamine, diisopropylamine and such like, alone or in combinations thereof.

The initiator is a combination of dialkylamins and trialkylamines which are supported or bound on polymers.

The solvents for dissolving NCA are selected from dimethyl formamide, dimethyl sulphoxide, dichloro methane, dioxane, alone or in combinations thereof. The NCA are dissolved in the solvent at temperatures ranging from 0-80° C.

The molecular weight of the copolymer-1 of the invention is as shown in FIG. 1. The molecular weight is less than 20 KDa varying between 8 and 19 KDa. The graph in FIG. 1 indicates that % of copolymer-1 below 2 KDa to be 0.25% and % over 40 KDa to be 0.55%. The % of species in the range of 8-19 KDa is 99.25%. Since the range of copolymer-1 above 20 KDa is below is less than 1%, the copolymer-1 is non-toxic as exemplified in example II in U.S. Pat. No. 6,620,847 to Konfino et al.

The following examples are given by way of illustration and therefore should not construed to limit the scope of the present invention.

Example 1

Synthesis of NCA of O-Benzyl Tyrosine

An oven dried 250 ml Schlenk flask was cooled under vacuum and charged with argon, 1 gm of O-Benzyl Tyrosine was added to the flask. To this Dry THF (20 ml) was added and stirred 0 0.30 gm of triphosgene was added and the reaction mixture was refluxed for 4 hours for 55° C. under argon atmosphere. After refluxing, the reaction mixture was filtered through frit. The resulting residue was dissolved in 40 ml of dry hexane. The resulting suspension stored at −20° C. overnight to assure complete crystallization. The NCA was recrystallized from THF/Hexane. The yield of NCA of O-Benzyl Tyrosine was 75%.

Example 2

Synthesis of NCA of $N^\epsilon$ Triflouroacetyl Lysine

An oven dried 250 ml Schlenk flask was cooled under vacuum and charged with argon, 1 gm. of $N^\epsilon$Triflouroacetyl Lysine was added to the flask. To this dry dioxane (20 ml) was added and stirred 0.40 gm of triphosgene was added and the reaction mixture was refluxed for 4 hours for 55° C. under argon atmosphere. After refluxing, the reaction mixture was filtered through frit. The resulting residue was dissolved in 40 ml of dry hexane. The resulting suspension stored at −20° C. overnight to assure complete crystallization. The NCA was recrystallized from dioxane/hexane. The yield of NCA of $N^\epsilon$Triflouroacetyl Lysine was 93%.

Example 3

Synthesis of NCA of L-Alanine

An oven dried 250 ml Schlenk flask was cooled under vacuum and filled with argon. 2 gm (22.4 mmol) of L-Alanine and 1.39 g (7.49 mmol) of triphosgene were added to the flask. To this 30 ml of dry THF was added and the reaction mixture was refluxed at 50° C. for about 3 hours under argon atmosphere. The mixture was then filtered through frit to remove insoluble ones and the filtrate was then added into 70 ml of n-hexane and the resulting suspension stored at −20° C. overnight to ensure complete crystallization. The yield of NCA of L-Alanine was 45%.

Example 4

Synthesis of NCA of g-Benzyl Glutamate

An oven dried 250 ml Schlenk flask was cooled under vacuum and charged with argon. 2 gm of (8.43 m mol) of g-benzyl glutamate and 0.834 gm. (2.81 mmol) of triphosgene were added to the flask and the reaction mixture was refluxed for about 3 hours. The reaction mixture was filtered through frit to remove insoluble ones and the filtrate was then added into 70 ml of dry n-hexane and resulting suspension stored at −20° C. overnight to ensure complete crystallization. The yield of NCA of g-benzyl glutamate was 75%.

Example 5

Synthesis of Copaxane

Copaxane 1 was prepared from N-carboxyanhydrides of tyrosine, alanine, γ-benzyl glutamate and $N^\epsilon$-trifluoroacetyllysine. The polymerization reaction was carried out at room temperature in anhydrous dioxane with polymer supported diethyl amine as initiator for 24 hrs.

Protected copolymer-I was treated with 33% HBr in acetic acid which removed the O-benzyl from Tyrosine and gamabenzyl protecting group from 5-carboxylate of the glutamate residue. 2 g of trifluoroacetyl-copolymer-I was dispersed in 100 ml of water to which 5 g of (IM) piperidine was added. The mixture was stirred for 24 hours at room temperature. The solution of crude copolymer-I was distributed into dialysis bags and dialyzed at 15° C., against water until a pH=8 are attained. It was then dialyzed against 0.3% acetic acid and again water until pH=5.5-6.0 was obtained. This solution was then concentrated and lyophilized to dryness. These copolymers were used for characterization.

Example 6

Synthesis of Copaxane

Copaxane 1 was prepared from N-carboxyanhydrides of tyrosine, alanine, γ-benzyl glutamate and $N^\epsilon$-trifluoroacetyllysine. 1.5 mMole of NCA of L-Alanine, 0.46 mMole of NCA of γ-benzyl glutamate, 0.28 mMole of NCA of o-benzyl 1-tyrosine and 0.278 mMole of NCA of $N^\epsilon$-trifluoroacetyllysine were reacted with 0.001 mMole of styrene divinyl benzene copolymer supported diethylamine at room temperature in anhydrous dioxane under stirring for 24 hrs to obtain the protected copolymer-I. Protected copolymer-I was treated with 1 ml of 33% HBr in acetic acid which removed the O-benzyl from Tyrosine and gama-benzyl protecting group from 5-carboxylate of the glutamate residue. 2 g of trifluoroacetyl-copolymer-I was dispersed in 100 ml of water to which 5 g of (IM) piperidine was added. The mixture was stirred for 24 hours at room temperature. The solution of crude copolymer-I was distributed into dialysis bags and dialyzed at 15° C., against water until a pH=8 was attained. It was then dialyzed against 0.3% acetic acid and again water until pH=5.5-6.0 was obtained. This solution was then concentrated and lyophilized to dryness. These copolymers were used for characterization.

Example 7

Synthesis of Copaxane

Copaxane 1 was prepared from N-carboxyanhydrides of tyrosine, alanine, γ-benzyl glutamate and $N^\epsilon$-trifluoroacetyllysine. 1.5 mMole of NCA of L-Alanine, 0.46 mMole of NCA of γ-benzyl glutamate, 0.28 mMole of NCA of o-benzyl 1-tyrosine and 0.278 mMole of NCA of $N^\epsilon$-trifluoroacetyllysine were reacted with 0.028 mMole of styrene divinyl benzene copolymer supported diisopropylamine at room temperature in anhydrous dioxane under stirring for 24 hrs to obtain the protected copolymer-I.

Protected copolymer-I was treated with 3 ml of 33% HBr in acetic acid which removed the O-benzyl from Tyrosine and gama-benzyl protecting group from 5-carboxylate of the glutamate residue. 2 g of trifluoroacetyl-copolymer-I was dispersed in 100 ml of water to which 5 g of (IM) piperidine was added. The mixture was stirred for 24 hours at room temperature. The solution of crude copolymer-I was distributed into dialysis bags and dialyzed at 15° C., against water until a pH=8 was attained. It was then dialyzed against 0.3% acetic acid and again water until pH=5.5-6.0 was obtained. This solution was then concentrated and lyophilized to dryness. These copolymers were used for characterization.

Example 8

Elution volume (in μL) was plotted against refractive index (in au) to show that the molecular weight of the copolymer-1 synthesized by the process of the invention was between 8-19 KDa as shown in FIG. 1.

The advantages of present invention are:
i. An important advantage of the invention is the used of non-toxic heterogeneous polymer-supported catalysts that are easy to handle, use and separate from the reaction mixtures.
ii. It provides simple and efficient process, using commonly available chemicals and result in the product directly, with a high degree of purity.
iii. It provides a co-polymer which has no residues of acids.
iv. The process used in present invention does not require any more steps for separation, purification, fractionation of various molecular weight ranges and such like.
v. The polymer-supported catalysts catalyse the polymerization reaction to longer chain lengths. The polymer molecule weight is in the range of 15000-19000 Daltons.
vi. These catalysts control the synthesis of the polypeptide such that molecular weights of the product can be obtained specified weight range.
vii. Polypeptides obtained by using the catalysts have narrow molecule weight distribution.
viii. The concentrations of the catalysts required for the reactions are 10× less than the conventional homogenous catalysts.

The invention claimed is:

1. A process for the synthesis of copolymer-1 having a molecular weight below 20 KDa and acid content of less than 1%, the process comprising:
   a) dissolving N-carboxyanhydrides (NCA) of tyrosine, alanine, γ-benzyl glutamate and $N^\epsilon$-trifluoroacetyllysine in a solvent;
   b) polymerizing the NCA by initiating with a polymer-supported dialkylamine or a polymer-supported trialkylamine or both, followed by stirring at room temperature to obtain copolymer 1;
   c) pouring the copolymer-1 as obtained in step b) into water, filtering the product followed by washing with water and drying;
   d) suspending the dried copolymer-1 as obtained in step c) in acetic acid, adding HBr in acetic acid, stirring at room temperature, decanting the acetic acid and evaporating;
   e) dispersing the copolymer-1 as obtained in step d) in water, adding 1 M piperidine, stirring for a time period in the range of 20-28 hrs at room temperature to form a solution;
   f) dialyzing the solution as obtained in step e) at room temperature to achieve pH=8;
   g) dialyzing the solution as obtained in step f) against acid followed by water to achieve pH=5.5-6 followed by concentrating the solution to obtain concentrated copolymer-1;
   h) lyophilizing the solution as obtained in step g) to dryness.

2. The process for the synthesis of copolymer-1 as claimed in claim 1, wherein said solvent is selected from group comprising dimethyl formamide, dimethyl sulphoxide, dichloromethane, dioxane and combinations thereof.

3. The process for the synthesis of copolymer-1 as claimed in claim 1, wherein the supported dialkylamine used as initiator is selected from the group consisting of dimethylamine, diethylamine, diisopropylamine and combinations thereof.

4. The process for the synthesis of copolymer-1 as claimed in claim 1, wherein the polymer-supported initiator is a trialkyl amine alone or in combination with said polymer-supported dialkylamine.

5. A method for treating a subject suffering from multiple sclerosis, said method comprising:
   a) dissolving N-carboxyanhydrides (NCA) of tyrosine, alanine, γ-benzyl glutamate and $N^\epsilon$-trifluoroacetyllysine in a solvent;
   b) polymerizing the NCA by initiating with a polymer-supported dialkylamine or a polymer-supported trialkylamine or both, followed by stirring at room temperature to obtain copolymer 1;
   c) pouring the copolymer-1 as obtained in step b) into water, filtering the product followed by washing with water and drying;
   d) suspending the dried copolymer-1 as obtained in step c) in acetic acid, adding HBr in acetic acid, stirring at room temperature, decanting the acetic acid and evaporating;
   e) dispersing the copolymer-1 as obtained in step d) in water, adding 1 M piperidine, stirring for a time period in the range of 20-28 hrs at room temperature to form a solution;
   f) dialyzing the solution as obtained in step e) at room temperature to achieve pH=8;
   g) dialyzing the solution as obtained in step f) against acid followed by water to achieve pH=5.5-6 followed by concentrating the solution to obtain concentrated copolymer-1;
   h) lyophilizing the solution as obtained in step g) to dryness, thereby producing copolymer-1 having a molecular weight below 20 kD and an acid content below 1%;
   and administering said copolymer-1 produced by steps (a) through (h) to said subject.

* * * * *